United States Patent [19]
Gillies et al.

[11] Patent Number: 5,880,146
[45] Date of Patent: Mar. 9, 1999

[54] INHIBITION OF IL-12-INDUCED IFN-γ SYNTHESIS BY SPECIFIC BIS-PHENOL COMPOUNDS AS A METHOD OF IMMUNE MODULATION

[75] Inventors: Stephen D. Gillies, Carlisle; John Wesolowski, Weymouth, both of Mass.

[73] Assignee: Fuji ImmunoPharmaceuticals Corporation, Lexington, Mass.

[21] Appl. No.: 473,364

[22] Filed: Jun. 7, 1995

[51] Int. Cl.$^6$ .......................... A61K 31/38; A61K 31/35
[52] U.S. Cl. .......................... 514/437; 514/454; 514/716; 514/717; 514/718; 514/721; 514/728; 514/731; 514/732; 514/734
[58] Field of Search .................................... 514/437, 454, 514/716, 717, 718, 721, 728, 731, 732, 734

[56] References Cited

U.S. PATENT DOCUMENTS 5,185,377  2/1993  Schewe et al. .......................... 514/721

FOREIGN PATENT DOCUMENTS 0 433 827 A2  9/1990  European Pat. Off. .
0 583 665 A2  7/1993  European Pat. Off. .

OTHER PUBLICATIONS

Jontell et al., "Effects of Unpolymerized Resin Components on the Function of Accessory Cells Derived from the Rat Incisor Pulp," *J. of Dental Research,* 74:1162–1167 (1995).

Correale et al. (1995), "Patterns of Cytokine Secretion by Autoreactive Proteolipid Protein–Specific T Cell Clones During the Course of Multiple Sclerosis," 154 *The Journal of Immunology,* 2959–2968.

Germann et al. (1995), "Administration of Interleukin 12 in Combination with Type II Collagen Induces Severe Arthritis in DBA/1 Mice," 92 *Proc. Natl. Acad. Sci. USA;* 4823–4827.

Article Abstract (1993), "Interferon Beta–1b is Effective in Relapsing–Remitting Multiple Scherosis. I. Clinical Results of a Multicenter, Randomized, Double–Blind, Placebo–controlled Trial," 43 *Neurology;* 655–661.

Mosmann et al. (1989), "TH1 and TH2 Cells: Different Patterns of Lymphokine Secretion Lead to Different Functional Properties," 7 *Ann. Rev. Immunol.;* 145–173.

*Primary Examiner*—Joseph McKane
*Attorney, Agent, or Firm*—Testa, Hurwitz & Thibeault, LLP

[57] ABSTRACT

Disclosed are chemical agents for modulating certain cellular immune reactions that can lead to autoimmune disorders. By specific modulation, harmful immune reactions can be lessened in severity or even prevented without resorting to potentially dangerous general immune suppression. The described chemical agents inhibit IL-12 induction of the secretion of key immune modulators. The described chemical agents are specific inhibitors of IL-12 induced Th1 immune response.

10 Claims, 3 Drawing Sheets

INHIBITION OF IL-12-INDUCED IFN-γ SYNTHESIS BY SPECIFIC BIS-PHENOL COMPOUNDS AS A METHOD OF IMMUNE MODULATION

BACKGROUND OF THE INVENTION

Autoimmune diseases result from the recognition of "self" by the immune system followed by a humoral (antibody) or cell-mediated response that leads to the destruction of the one's own cells. While a healthy immune system selects against self-reactive immune cells (T cells and B cells) in the thymus by quickly destroying them, this system is imperfect. When self-reactive cells are released into the circulation and penetrate into peripheral tissues they may encounter the self antigen to which they can respond. These antigens are displayed on the surface of cells in the form of peptide fragments, non-covalently associated with either class I or class II antigen molecules of the major histocompatibility complex (HLA in humans). Fortunately, this first encounter of self reactivity generally results in a weak response. This is because multiple signals are required to stimulate a proliferative response that both activates the effector function of the cell and increases its number by cell division. Without a second co-stimulatory signal, which is found on professional antigen-presenting cells (APC), the T cell becomes non-reactive (or anergic) to a second exposure to the same antigen and a harmful reaction is prevented.

How this protective system breaks down in autoimmune disease is under intense investigation and many associations have been made between specific types of immune responses and disease activity. For example, conditions that lead to the up-regulation of HLA molecules in the central nervous system (CNS), and increased antigen presentation, have been associated with the T-cell mediated destruction of nervous tissue in multiple sclerosis (MS) patients. While the exact triggering event is unknown, a clear picture is emerging as to how the immune system regulates such responses. One of the key immune regulators is the T helper cell which reacts to antigens presented on HLA class II molecules. This $CD4^+$ cell differentiates in response to antigenic stimulation and becomes a type 1 or type 2 helper (Th1 or Th2) according to the type of cytokines that it secretes (Mosmann and Coffman, Ann. Rev Immunol. 7:145). A Th1 response leads to the secretion of interleukin-2 (IL-2) and interferon-γ (IFN-γ) which stimulates cell-mediated immune reactions against intracellular pathogens. A Th2 response leads to the secretion of IL4, IL-5 and IL-10 which stimulates antibody responses to extracellular pathogens. The most interesting component of this system of regulation is that one response inhibits the other through the negative regulatory activities of the cytokines that are produced. Thus, IL-4 and IL-10 can down-regulate Th1 responses while IFN-γ can down-regulate Th2 responses.

The importance of such a regulatory feedback loop in autoimmune disease recently has been associated with disease activity in multiple sclerosis. T cells cloned from patients undergoing active disease have been shown to produce TH1 cytokines upon stimulation with antigen in vitro (Correale et al. J. Immunol. 154:2959). T cell clones obtained from the same patient during the remission phase produce Th2 cytokines. They also produce another potent suppressor of cell-mediated immunity, tumor growth factor β (TGF-β).

The regulatory activity of T helper cells and their differentiation following exposure to antigen is regulated by cytokines as well. IL-12 has been shown to be essential in the generation of Th1 cells. IL-12 is released primarily by the antigen presenting cell, which for Th1 responses is normally a macrophage (reviewed by Trinchieri, Blood 84:4008). Other cytokines also are secreted by the responding T cell after antigen stimulation, especially IL-2. Cytokines IL-12 and IL-2 have a powerful synergistic effect in the induction of IFN- from both T helpers and natural killer (NK) cells (Eur. Patent Appl. 90123670.3). This secreted IFN-γ then inhibits any Th2 cell proliferation and polarizes the response to favor cell-mediated immunity (the Th1 response). If IL4 was the major cytokine present during antigen stimulation, a Th2 response would be made and the Th1 response would be inhibited. Thus, the initiating event that establishes the cytokine environment has an important role in determining the nature of the immune response. Another consequence of the Th phenotype is reflected in the isotype of antibody that is made in response to an antigen. TH1 responses lead to increases in cytolytic antibodies, i.e., those capable of mediating antibody-dependent cellular cytotoxicity (ADCC) and those that activate the complement system. Th2 responses lead to the production in non-cytolytic classes (isotypes) of antibodies. The importance of this phenomenon has recently been described in mouse models of collagen-induced arthritis where Th1 responses induced by IL-12 favored the production of IgG2a (cytolytic) over IgG1 (non-cytolytic) and this class switching correlated with disease occurrence and severity (Germann et al., Proc. Natl. Acad. Sci. 92:4823).

It is one object of this invention to provide compositions for antagonizing the IL-12 induced activities of immune cells. It is another object of this invention to provide a method for antagonizing IL-12 induced activities of T helper cells so as to inhibit the IFN-γ induced Th1 response, be effective to modulate the induction of Th2 cells; be effective to inhibit a cellular immune response; and/or be effective to stimulate the production of Th2 cytokines including IL-4, IL-5, and L-10. It is still another object of the invention to provide a method for stimulating the cellular production of cytokines in immune cells, which can be immune cells in a mixed or selected population of cells in an in vitro cell culture or can be circulating immune cells in a mammal. It is still another object of the invention to provide an in vitro diagnostic for measuring IL4 production in peripheral blood mononuclear cells.

SUMMARY OF THE INVENTION

Certain bis phenol or phenoxy compounds, and derivatives thereof, have been discovered to antagonize the IL-12 mediated induction of IFN-γ synthesis. The bis-compounds also have been discovered to be therapeutically useful in the stimulation of the immune system to inhibit the IL-12 induced production of IFNγ and thereby to modulate induction of Th2 cells. Inhibition of IFNγ production can inhibit the induction of Th1 immune cells, and/or inhibit a cellular immune response. Modulation of the induction of Th2 cells can lead to stimulation of the secretion of Th2 cytokines including IL-4, IL-5, and IL-10, to stimulation of the Th2 immune response against extracellular pathogens, and to the induction of antibody synthesis.

In one aspect, the invention is embodied as a composition for antagonizing IL-12 induced immune response. The composition comprises a pharmaceutically acceptable carrier and a bis-compound having the following general formula.

The X is optional, and if present, is —O—, —S—, or —CH$_2$—. At least one of R$_1$, R$_2$, R$_3$, and R$_4$, and at least one of R$_7$, R$_8$, R$_9$, and R$_{10}$, is OR__, where R$_{13}$ is H or lower alyl. R$_5$ and R$_6$ are selected independently from H, C$_1$–C$_{12}$ branched or linear hydrocarbons, phenyl, phenyl substituted with halo, nitro, carboxy, alkoxy, hydroxy, alkoxy carbonyl, or alkyl, alkyl substituted with halo, nitro, carboxy, alkoxy, hydroxy, or alkoxy carbonyl, or alkenyl, alkenyl substituted with halo, nitro, carboxy, alkoxy, hydroxy, or alkoxy carbonyl. Each of R$_1$, R$_2$, R$_3$, R4, R$_7$, R$_8$, R$_9$, and R$_{10}$ which is not OR$_{13}$ is independently hydrogen, halo orlinear orbranched lower alkyl. A lower alyl means an alkyl group having 1 to 6 carbon atoms.

In another aspect, the invention is embodied as a composition for antagonizing the IL-12 induced immune response. The composition comprises a pharmaceutically acceptable carrier and a bis-compound having the following general formula.

At least one of R$_1$, R$_2$, R$_3$, R$_4$, and R$_{11}$ and at least one of R$_7$, R$_8$, R$_9$, R$_{10}$ and R$_{12}$, is OR$_{13}$, where R$_{13}$ is H or lower alkyl. R$_5$ and R$_6$ are selected independently from H, C$_1$–C$_{12}$ branched or linear hydrocarbons, phenyl, phenyl substituted with halo, nitro, carboxy, alkoxy, hydroxy, alkoxy carbonyl, or alkyl, alkyl substituted with halo, nitro, carboxy, alkoxy, hydroxy, or alkoxy carbonyl, or alkenyl, alkenyl substituted with halo, nitro, carboxy, aLkoxy, hydroxy, or alkoxy carbonyl. Each of R$_1$, R$_2$, R$_3$, R$_4$, R$_7$, R$_8$, R$_9$, R$_{10}$, R$_{11}$ and R$_{12}$ which is not OH or OR$_{13}$ is independently hydrogen, halo or linear or branched lower alkyl.

Preferably, at least one of R$_1$, R$_2$, R$_3$, R$_4$, R$_{11}$ and at least one of R$_7$, R$_8$, R$_9$, R$_{10}$, R$_{12}$ is OH. One or both of R$_5$ and R$_6$ can be H or a hydrocarbon radical having 1 to 12 carbon atoms. More preferably, one of R$_5$ and R$_6$ is H and the other is a linear or branched aLkyl chain having 1 to 12 carbon atoms. Each R$_1$, R$_2$, R$_3$, R$_4$, R$_7$, R$_8$, R$_9$, R$_{10}$, R$_{11}$ and R$_{12}$ which is not OH can be independently hydrogen, methyl, ethyl, propyl, isopropyl, butyl, tertiary-butyl, or linear or branched pentyl.

In another aspect the invention is embodied as a method of antagonizing the IL-12 mediated induction of IFN-γ synthesis in a mammal comprising the step of administering to a mammal one of the above described bis-compounds in an amount effective to antagonize IL-12 mediated induction of IFN-γ synthesis. nhibition of IL-12 induced IFNγ synthesis can have the effect of inhibiting the induction of Th1 cells; modulating the induction of Th2 cells; inhibiting a cellular immune response, and/or stimulating the production of Th2 cytokines including IL-4, IL-5, or IL-10.

In another aspect, the invention provides a method of antagonizing IL-12 in immune cells comprising contacting immune cells with a bis-compound, described above, in an amount sufficient to inhibit IL-12 induced production of IFN-γ. The immune cells which are contacted with the bis-compound can be a mixed population of cells in an in vitro cell culture, or can be a mixed population of cells which are circulating in a mammal.

DETAILED DESCRIPTION OF THE INVENTION

The natural mechanism for combating inappropriate cell-mediated responses may be to suppress them with a Th2-like response. The inhibition of IFN-γ, which is normally produced in the Th1 response, would then block many of its potentially harmful effects including the activation of macrophage, natural killer cells and cytolytic T cells, and the induction of class I and class II HLA in the target tissue.

The importance of such a "suppressor" effect in diseases such as MS is suggested by the finding that IFN-β, a molecule that down regulates the class II HLA induced by IFN-γ, reduces the number of relapses and the extent of central nervous system (CNS) inflammation (The IFNB Multiple Sclerosis Study Group, Neurology 43:655). The general immunosuppressing drug cyclosporine, on the other hand, can lessen autoimmune disease while it is administered, but increases its severity once the drug is withdrawn (Sorokin et al. J. Exp. Med. 164:1615). This is likely the result of inhibiting the suppressor effect as well as the undesirable cell-mediated response, such that the destructive response quickly returns, unchecked, as soon as the general immunosuppressing drug is no longer present.

One way of changing the outcome of an immune response would be to administer the appropriate cytokine at the time of antigen stimulation. The problem with this approach is that the systemic administration of cytokines is difficult due to their very short circulating half-lives, their deleterious side effects, and their high cost of manufacture. Another approach is to identify small chemical inhibitors of either Th1 or Th2 cytokines so that the effective concentration of the non-inhibited cytokines is increased. For example, inhibitors of IL-12 secretion or IL-12 induced activities, e.g., the induction of IFN-γ, could selectively block cell-mediated immunity by preventing hl development. If this is done without inhibiting Th2 responses, then the produced Th2 cells could serve as suppressors of ongoing or future Th1 responses to the same antigen, as described above for MS (Corealle et al. (1995) J. Immunol., 154:2959–2968). This type of modulation of an immune response serves to stimulate the body's own protective mechanism against autoimmunity rather than suppressing the immune system altogether.

The present invention describes methods that can be used to identify small molecule inhibitors of Th1 immune responses that are not generally immunosuppressive, and discloses a claim of such selectively immunosuppressive compounds and compositions. The methods for synthesizing useful embodiments of the invention are described as well as assays useful for testing their pharmacological activities both in vitro and in pre-clinical in vivo animal models. The instant invention provides to derivatives of bis-compounds of the general formulae described herein.

Compounds which are particularly effective for each of these purposes include substituted bis-compounds and particularly bis-phenols which are described in detail herein. The terms "bis-compound(s)" and "bis-phenol compound" will be used herein to include all substituted bis-compounds herein described, and generally define a molecular structure comprising a variously substituted central carbon atom flanked by a pair of phenol or phenoxy groups, optionally derivatized as disclosed herein.

An effective amount of the bis-compound comprises an amount of the individual agent such that the desired clinical endpoint, antagonization of IL-12 induced immune response, is reached. The amount to be administered will depend on the potency, bioavailability, in vivo half-life, and toxicity of the individual compound. In general, the dose would reasonably be expected to range between 0.1 to 100 mg/kg per adult per administration, and preferably would be between 1 to 20 mg/ kg per adult per administration.

The language "therapeutically effective amount" is intended to include the amount or concentration of bis-compound sufficient to antagonize the IL-12 induced immune response activities, such as inhibition of IFNγ. A therapeutically effective amount can be determined on an individual basis and will be based, at least in part, on consideration of the severity of the symptoms to be treated. Further, the effective amounts of the bis-compound may vary according to age, sex, and weight of the subject being treated. A therapeutically effective amount of a given bis-compound can be determined by one of ordinary skill in the art employing such factors described herein using no more than routine experimentation in clinical management.

In the preferred embodiments of each aspect of the present invention, the composition of bis-compound is prepared together with a pharmaceutically acceptable carrier substance for oral ingestion or parenteral injection. The language "pharmaceutically acceptable carrier" is intended to include substances capable of being co-administered with the bis-compound and which allows the compound to perform its intended function of antagonizing IL-12. Examples of pharmaceutically acceptable carriers are commercially available inert gels or liquids. Gels comprise of the compound, a base selected from oleaginous base, water or emulsion-suspension base, and a gelling agent, such as hydroxypropyl cellulose, acrylic acid polymers, and the like. Liquids include emulsions, solutions, and suspensions. The term, "pharmaceutically acceptable salts" is intended to include salts which are recognized in the art. Typically these salts are capable of being hydrolyzed under physiological conditions. Examples of such salts include sodium, potassium, and hemisulfate. Additionally, a carrier having effective bioavailability should be used in preparations of the compound for oral ingestion.

The present invention further relates to pharmaceutical compositions containing the above noted bis-compounds and appropriate pharmaceutically acceptable excipients, oils such as corn oil, buffers such as PBS, saline, ethanol, polyethylene glycol, glycerin, polypropylene glycol, dimethylsulfoxide, and amide such a dimethylacetamide, proteins such as albumin, a detergent such as Tween 80, mono-, oligo-, or polysaccharides, such as glucose, lactose, cyclodextrins and starch.

The composition may take forms such as suspensions, solutions, or emulsions in oily or aqueous vehicles, and may contain formulating agents, such as suspending, stabilizing, or dispersing agents, isotonic agents and/or dissolving co-solvents conventionally cited in the pharmaceutical art.

The term "subject" is intended to include all mammals such as humans, dogs, cats, horses, cows, goats, rats and mice.

The amounts of bis-compound incorporated into the formulation of the present invention is not critical; the concentration should only be in a range sufficient to permit ready application of the formulation in an amount which will deliver the desired amount of bis-compound.

Bis-phenol compounds are commercially available from chemical suppliers. Substituted bis-phenol compounds may be readily made by one of ordinary skill in the art using generally known synthesis techniques. (See for example, Marsh et al., 1949, *J. Industrial and Engineering Chemistry,* vol. 41, pp. 2176–2184; Beaver et al., 1952, *J. Amer. Chem. Soc.,* vol. 74, pp. 3410–3411). Exemplary syntheses of bis-phenol compounds are presented below and are not meant to be limiting.

Exemplary Synthesis of Bis-Compounds

Exemplary Synthesis #1

To a solution of 2,4-dimethyl phenol (24.6 g; 0.2 mol) in $CH_3CO_2H$ (40 ml) and $H_2SO_4$ (6 ml) cooled with an ice-water bath was added 3,5,-trimethylhexanal (17.1 g; 0.12 mol) in $CH_3CO_2H$ (10 ml) under stirring. The mixture was stirred at room temperature for 10 hrs. The reaction mixture was poured into ice water. The white solid which formed was filtered and washed repeatedly with aqueous ethanol. Recrystallization from aqueous ethanol provided 17.0 g of bis-1,1-[2-hydroxy-3,5-dimethylphenyl]-3,5,5-dimethyl hexan, which has a melting point (m.p.) of 168° C.).

Exemplary Synthesis #2

To a solution of 2-chloro 4-methyl phenol (28.5 g; 0.2 mol) in $CH_3CO_2H$ (40 ml) and $H_2SO_4$ (6 ml) was added nonyl aldehyde (16g) in $CH_3CO_2H$ (5 ml) under stirring. The mixture was stirred at 80° C. overnight. The reaction mixture was poured into ice water and extracted three times with ethyl acetate. The combined organic phases were washed with 10% $NaCO_3$ and brine, dried, filtered through a pad of silica gel 60. Chromatography (10% ethyl acetate in hexane) provided 12.4 g of pure bis-1,1-[2-hydroxy-3-chloro-5-methylphenyl]nonane, which has a m.p. of 127° C.

A significant number of bis-compounds have been synthesized, and the chemical formula of these compounds is presented in tabular form in Table 1 below. R1—R12 correspond to those symbols in the structural formulae set forth above.

TABLE 1

| | | Bis-compounds | | | | |
|---|---|---|---|---|---|---|
| | R1 | R2 | R3 | R4 | R5 | R6 |
| 53433 | H | OH | t-(CH3)3C | H | CH3 | CH3 |
| 53437 | H | OH | t-C8H17 | H | CH3 | CH3 |
| 54372 | H | OC4H7 | t-C8H17 | H | CH3 | CH3 |
| 51850 | OH | CH3 | H | CH3 | H | H |
| 51851 | OH | CH3 | H | CH3 | H | n-C3H7 |
| 54013 | OH | CH3 | H | CH3 | H | isoC3H7 |
| 51852 | OH | CH3 | H | CH3 | H | C7H16 |
| 51853 | OH | CH3 | H | CH3 | H | C8H17 |
| 54015 | OH | CH3 | H | CH3 | H | C6H13 |
| 54019 | OH | CH3 | H | CH3 | H | C5H11 |
| 8302 | OH | CH3 | H | CH3 | H | C9H19 |
| 54005 | OH | t-C4H9 | H | CH3 | H | CH3 |
| 54008 | OH | t-C4H9 | H | CH3 | H | C2H5 |
| 54016 | OH | t-C4H9 | H | CH3 | H | C2H6-Ph |
| 54011 | OH | t-C4H9 | H | CH3 | H | Ph |
| 54018 | OH | t-C4H9 | H | CH3 | H | C5H11 |
| 54020 | OH | t-C4H9 | H | CH3 | H | C4H9 |
| 54014 | OH | t-C4H9 | H | CH3 | H | nC6H13 |
| 54011 | OH | t-C4H9 | H | CH3 | H | nC7H15 |
| 54030 | OH | t-C4H9 | H | T-C4H9 | H | H |
| 54332 | OH | t-C4H9 | H | T-C4H9 | H | C2H5 |
| 54107 | OH | t-C4H9 | H | T-C4H9 | H | CH3 |
| 54002 | OH | t-C4H9 | H | T-C4H9 | H | C3H7 |
| 54040 | OH | t-C4H9 | H | T-C4H9 | H | C4H9 |
| 54047 | OH | t-C4H9 | H | T-C4H9 | H | Ph |
| 54041 | OH | t-C4H9 | H | T-C4H9 | H | n-C7H15 |
| 54333 | OH | C(CH3)3—CH2CH3 | H | C(CH3)2—CH2CH3 | H | C3H7 |
| 8296 | OH | CH3 | H | Cl | H | H |
| 60109 | H | t-C4H9 | OH | t-C4H9 | H | H |
| 54085 | H | t-C4H9 | OH | t-C4H9 | H | CH3 |
| 54029 | H | t-C4H9 | OH | t-C4H9 | H | C2H5 |
| 54032 | H | t-C4H9 | OH | t-C4H9 | H | nC3H7 |
| 54051 | H | t-C4H9 | OH | t-C4H9 | H | Ph |
| 54055 | H | t-C4H9 | OH | t-C4H9 | H | Ph-pCO2H |
| 60634 | H | t-C4H9 | OH | t-C4H9 | CH3 | CH3 |
| 54483 | H | t-C4H9 | OH | H | H | isoC3H7 |
| 54093 | H | CH3 | OH | H | CH3 | CH3 |
| 54094 | H | CH3 | OH | H | C6H13 | CH3 |
| 54455 | H | CH3 | PH | H | C2H5 | C2H5 |
| 54096 | H | CH3 | OH | H | —(CH2)4— | —(CH2)4— |
| 54099 | H | CH3 | OH | H | nC3H7 | nC3H7 |
| 54453 | H | CH3 | OH | H | CH3 | isoButyl |
| 54454 | H | CH3 | OH | H | CH3 | isoC3H7 |
| 54063 | H | CH3 | OH | H | CH3 | nC3H7 |
| 54059 | H | CH3 | OH | H | CH3 | nC6H13 |
| 54009 | H | CH3 | OH | H | CH3 | C3H7 |
| 54003 | H | CH3 | OH | H | CH3 | C2H5 |
| 54061 | H | CH3 | OH | H | nC3H7 | nC3H7 |
| 54031 | H | CH3 | OH | H | CH3 | C2H5 |
| 54045 | H | CH3 | OH | H | C2H5 | C2H5 |
| 54048 | H | CH3 | OH | H | —(CH2)5— | —(CH2)5— |
| 54052 | H | CH3 | OH | H | CH3 | isoButyl |
| 54037 | H | CH3 | OH | CH3 | H | H |
| 54046 | H | CH3 | OH | CH3 | CH3 | CH3 |
| 54471 | H | CH3 | OH | CH3 | H | C2H5 |
| 54034 | H | CH3 | OH | CH3 | H | CH3 |
| 54028 | H | CH3 | OH | CH3 | C2H5 | C2H5 |
| 52782 | H | CH3 | OH | CH3 | CH3 | C4H9 |
| 54044 | H | CH3 | OH | CH3 | H | nC3H7 |
| 54098 | H | CH3 | OH | CH3 | H | isoC3H7 |
| 54056 | H | CH3 | OH | CH3 | CH3 | C2H5 |
| 54060 | H | CH3 | OH | CH3 | H | Ph |
| 54097 | H | CH3 | OH | CH3 | H | Ph-pCH3 |
| 54095 | H | CH3 | OH | CH3 | H | Ph-pBr |
| 54114 | H | CH3 | OH | CH3 | H | Ph-isoC3H7 |
| 54105 | H | CH3 | OH | CH3 | H | CCl3 |
| 54042 | H | CH3 | OH | CH3 | H | Ph-pCl |
| 54470 | H | CH3 | OH | CH3 | H | Ph-pOH |
| 54101 | H | CH3 | OH | CH3 | H | Ph-mNO2 |
| 54101 | H | CH3 | OH | CH3 | H | Ph-pNO2 |
| 54038 | H | CH3 | OH | CH3 | H | Ph-mOH(-pOCH3) |
| 54004 | H | CH3 | OH | CH3 | H | Ph-mOH(-pOH) |
| 54006 | H | CH3 | OH | CH3 | H | Ph-mOCH3(-pOH) |
| 54043 | H | CH3 | OH | CH3 | H | Ph-(—O(CH2)—O) |
| 54102 | H | CH3 | OH | CH3 | H | Ph-mOH |

TABLE 1-continued

Bis-compounds

| | | | | | | |
|---|---|---|---|---|---|---|
| 54064 | H | CH3 | OH | CH3 | CH3 | C3H7 |
| 54474 | H | CH3 | OH | CH3 | CH3 | isoButyl |
| 54028 | H | CH3 | OH | CH3 | C2H5 | C2H5 |
| 54035 | H | CH3 | OH | CH3 | p-tolyl | p-tolyl |
| 54046 | H | CH3 | OH | CH3 | CH3 | CH3 |
| 54049 | H | CH3 | OH | CH3 | H | Ph-mCl |
| 54050 | H | CH3 | OH | CH3 | H | Ph-p-CO2H |
| 54057 | H | CH3 | OH | CH3 | H | Ph-p-CO2CH3 |
| 54023 | H | CH3 | OH | CH3 | —(CH2)5— | —(CH2)5— |
| 54109 | H | iso-C3H7 | OH | CH3 | H | C2H5 |
| 54054 | H | t-C4H9 | OH | CH3 | CH3 | H |
| 54472 | H | t-C4H9 | OH | CH3 | H | C2H5 |
| 54346 | H | t-C4H9 | OH | CH3 | H | Ph-CO2H |
| 54022 | H | iso-C3H7 | OH | CH3 | isoC3H7 | H |
| 54021 | H | t-C4H9 | OH | CH3 | CH3 | CH3 |
| 54053 | H | t-C4H9 | OH | CH3 | H | Ph-p-NO2 |
| 54058 | H | t-C4H9 | OH | CH3 | H | Ph |
| 54012 | H | isoC3H7 | OH | H | H | C3H7 |
| 54017 | H | isoC3H7 | OH | H | H | isoC3H7 |
| 54109 | H | isoC3H7 | OH | H | H | C2H5 |
| 54007 | H | isoC3H7 | OH | H | H | Ph |
| 54024 | H | isoC3H7 | OH | H | H | CH3 |
| 8317 | H | CH3 | OH | CH3 | H | 2-ethyl 4,4 dimethyl-pentyl |
| 8335 | OH | CH3 | H | CH3 | H | C8H17 |
| 8334 | H | CH3 | OH | CH3 | H | C8H17 |
| 8316 | OH | H | Cl | CH3 | H | 2-methyl-4,4-dimethyl-pentyl |
| 51853 | OH | CH3 | H | CH3 | H | 2-methyl 4,4-dimethyl pentyl |
| 1 | OH | CH3 | H | CH3 | H | 2,6 dimethyl-hept-5-ene |
| 2 | OH | CH3 | H | CH3 | H | 2,6-dimethyl 6 methoxy-heptyl |
| 3 | OH | CH3 | H | CH3 | H | 2,6 dimethyl-heptyl |
| 4 | OH | CH3 | H | CH3 | H | 2,6 dimethyl-heptane |
| 5 | OH | CH3 | H | CH3 | H | 6 methoxy 2,6-dimethyl-heptane |
| 6 | OH | CH3 | H | CH3 | H | 2,6 dimethyl-hept-5-ene |
| 7 | H | CH3 | OH | CH3 | H | 2,6 dimethyl heptane |
| 8 | H | CH3 | OH | CH3 | H | 6 methoxy 2,6 dimethyl heptane |
| 9 | H | CH3 | OH | CH3 | H | 2,6 dimethyl-5-heptene |

| | R7 | R8 | R9 | R10 | R11 | R12 |
|---|---|---|---|---|---|---|
| 53433 | H | OH | t-(CH3)3C | H | | —O— |
| 53437 | H | OH | t-C8H17 | H | | —O— |
| 54372 | H | O-n-C4H7 | t-C8H17 | H | | —O— |
| 51850 | OH | CH3 | H | CH3 | H | H |
| 51851 | OH | CH3 | H | CH3 | H | H |
| 54013 | OH | CH3 | H | CH3 | H | H |
| 51852 | OH | CH3 | H | CH3 | H | H |
| 51853 | OH | CH3 | H | CH3 | H | H |
| 54015 | OH | CH3 | H | CH3 | H | H |
| 54019 | OH | CH3 | H | CH3 | H | H |
| 8302 | OH | CH3 | H | CH3 | H | H |
| 54005 | OH | t-C4H9 | H | CH3 | H | H |
| 54008 | OH | t-C4H9 | H | CH3 | H | H |
| 54016 | OH | t-C4H9 | H | CH3 | H | H |
| 54011 | OH | t-C4H9 | H | CH3 | H | H |
| 54018 | OH | t-C4H9 | H | CH3 | H | H |
| 54020 | OH | t-C4H9 | H | CH3 | H | H |
| 54014 | OH | t-C4H9 | H | CH3 | H | H |
| 54011 | OH | t-C4H9 | H | CH3 | H | H |
| 54030 | OH | t-C4H9 | H | t-C4H9 | H | H |
| 54332 | OH | t-C4H9 | H | t-C4H9 | H | H |
| 54107 | OH | t-C4H9 | H | t-C4H9 | H | H |
| 54002 | OH | t-C4H9 | H | t-C4H9 | H | H |
| 54040 | OH | t-C4H9 | H | t-C4H9 | H | H |
| 54047 | OH | t-C4H9 | H | t-C4H9 | H | H |
| 54041 | OH | t-C4H9 | H | t-C4H9 | H | H |
| 54333 | OH | C(CH3)2—CH2CH3 | H | C(CH3)2—CH2CH3 | H | H |

TABLE 1-continued

| | | | Bis-compounds | | | |
|---|---|---|---|---|---|---|
| 8296 | OH | CH3 | H | Cl | H | H |
| 60109 | H | t-C4H9 | OH | t-C4H9 | H | H |
| 54085 | H | t-C4H9 | OH | t-C4H9 | H | H |
| 54029 | H | t-C4H9 | OH | t-C4H9 | H | H |
| 54032 | H | t-C4H9 | OH | t-C4H9 | H | H |
| 54051 | H | t-C4H9 | OH | t-C4H9 | H | H |
| 54055 | H | t-C4H9 | OH | t-C4H9 | H | H |
| 60634 | H | t-C4H9 | OH | t-C4H9 | H | H |
| 54483 | H | t-C4H9 | OH | t-C4H9 | H | H |
| 54093 | H | CH3 | OH | H | H | H |
| 54094 | H | CH3 | OH | H | H | H |
| 54455 | H | CH3 | OH | H | H | H |
| 54096 | H | CH3 | OH | H | H | H |
| 54099 | H | H | OH | H | H | H |
| 54453 | H | H | OH | H | H | H |
| 54454 | H | H | OH | H | H | H |
| 54063 | H | H | OH | H | H | H |
| 54059 | H | H | OH | H | H | H |
| 54009 | H | CH3 | OH | H | H | H |
| 54003 | H | CH3 | OH | H | H | H |
| 54061 | H | CH3 | OH | H | H | H |
| 54031 | H | H | OH | H | H | H |
| 54045 | H | H | OH | H | H | H |
| 54048 | H | CH3 | OH | H | H | H |
| 54052 | H | CH3 | OH | H | H | H |
| 54037 | H | CH3 | OH | CH3 | H | H |
| 54046 | H | CH3 | OH | CH3 | H | H |
| 54471 | H | CH3 | OH | CH3 | H | H |
| 54034 | H | CH3 | OH | CH3 | H | H |
| 54028 | H | CH3 | OH | CH3 | H | H |
| 52782 | H | CH3 | OH | CH3 | H | H |
| 54044 | H | CH3 | OH | CH3 | H | H |
| 54098 | H | CH3 | OH | CH3 | H | H |
| 54056 | H | CH3 | OH | CH3 | H | H |
| 54060 | H | CH3 | OH | CH3 | H | H |
| 54097 | H | CH3 | OH | CH3 | H | H |
| 54095 | H | CH3 | OH | CH3 | H | H |
| 54114 | H | CH3 | OH | CH3 | H | H |
| 54105 | H | CH3 | OH | CH3 | H | H |
| 54042 | H | CH3 | OH | CH3 | H | H |
| 54470 | H | CH3 | OH | CH3 | H | H |
| 54001 | H | CH3 | OH | CH3 | H | H |
| 54101 | H | CH3 | OH | CH3 | H | H |
| 54038 | H | CH3 | OH | CH3 | H | H |
| 54004 | H | CH3 | OH | CH3 | H | H |
| 54006 | H | CH3 | OH | CH3 | H | H |
| 54043 | H | CH3 | OH | CH3 | H | H |
| 54102 | H | CH3 | OH | CH3 | H | H |
| 54064 | H | CH3 | OH | CH3 | H | H |
| 54474 | H | CH3 | OH | CH3 | H | H |
| 54028 | H | CH3 | OH | CH3 | H | H |
| 54035 | H | CH3 | OH | CH3 | H | H |
| 54046 | H | CH3 | OH | CH3 | H | H |
| 54049 | H | CH3 | OH | CH3 | H | H |
| 54050 | H | CH3 | OH | CH3 | H | H |
| 54057 | H | CH3 | OH | CH3 | H | H |
| 54023 | H | CH3 | OH | CH3 | H | H |
| 54109 | H | isoC3H7 | OH | CH3 | H | H |
| 54054 | H | t-C4H9 | OH | CH3 | H | H |
| 54472 | H | t-C4H9 | OH | CH3 | H | H |
| 54346 | H | t-C4H9 | OH | CH3 | H | H |
| 54022 | H | iso-C3H7 | OH | Ch3 | H | H |
| 54021 | H | t-C4H9 | OH | CH3 | H | H |
| 54053 | H | t-C4H9 | OH | CH3 | H | H |
| 54058 | H | t-C4H9 | OH | CH3 | H | H |
| 54012 | H | isoC3H7 | OH | H | CH3 | CH3 |
| 54017 | H | isoC3H7 | OH | H | CH3 | CH3 |
| 54109 | H | isoC3H7 | OH | H | CH3 | CH3 |
| 54007 | H | isoC3H7 | OH | H | CH3 | CH3 |
| 54024 | H | isoC3H7 | OH | H | CH3 | CH3 |
| 8317 | H | CH3 | OH | CH3 | H | H |
| 8335 | OH | CH3 | H | CH3 | H | H |
| 8334 | H | CH3 | OH | CH3 | H | H |
| 8316 | OH | H | Cl | CH3 | H | H |
| 51853 | OH | CH3 | H | CH3 | H | H |
| 1 | OH | CH3 | H | CH3 | H | H |
| 2 | OH | CH3 | H | CH3 | H | H |

TABLE 1-continued

| | | | Bis-compounds | | | |
|---|---|---|---|---|---|---|
| 3 | OH | CH3 | H | CH3 | H | H |
| 4 | OH | CH3 | H | CH3 | H | H |
| 5 | OH | CH3 | H | CH3 | H | H |
| 6 | OH | CH3 | H | CH3 | H | H |
| 7 | H | CH3 | OH | CH3 | H | H |
| 8 | H | CH3 | OH | CH3 | H | H |
| 9 | H | CH3 | OH | CH3 | H | H |

Compounds which antagonize IL-12 can be identified readily using the assays described below. The described in vitro Screening Assay provides for the rapid screening of large numbers of compounds for their ability to antagonize IL-12, as measured by the inhibition of IFN-γ production. The screening assay described below also may be automated. Compounds which are identified by the screening assay may then be screened by a Mixed Lymphocyte Reaction Assay to analyze the compound further for its activity as either a general immune cell suppressor or as an inhibitor of IL-12 induced production of a Th1 immune response. Promising compounds, those which are not general immune suppressors, are tested for in vivo toxicity in rats.

The invention is illustrated further by the following non-limiting examples:

Example 1 Screening Assay for Compounds which Inhibit IL-12 Induction of IFN-γ.

Human peripheral blood monocytes (PBMC) were obtained from commercial sources as a leukophoresis from a healthy volunteer and were purified by centrifugation on a Ficoll-Hypaque (Pharmacia) gradient (1700 rpm for 20 min). The "buffy" coat containing the PBMC was diluted with serum-free culture medium (SF-RPMI) to a volume of 50 ml and collected by centrifugation at 1500 rpm for 5 min. Cells were resuspended in cell culture medium containing 10% fetal bovine serum (RPMI-10) and phytohemaglutinin (PHA - 10 μg/ml) at a density of 5×10⁶ cells/ml and were cultured for 3 days at 37° C. in a humidified $CO_2$ incubator. The PHA-activated cells were collected by centrifugation, washed three times with an equal volume of SF-RPMI and resuspended in fresh RPMI-10 (1×10⁶ cells /ml). Aliquots (100 μl) were dispensed into the wells of multiple 96-well plates to give a final cell number of 10⁵ per well. Test compounds, dissolved in dimethyl sulfoxide (DMSO) at 1 mg/ml, were first diluted in culture medium to an intermediate concentration of 20 μg/ml and then were added (50 μ/well) to a specific well of the plate for each compound. Stimulation medium (50 μl/well) containing 10% serum, IL-2 and IL-12 was added to final concentrations of 25 U/ml and 0.5 ng/ml, respectively. Control wells receive no IL-2 or IL-12 (negative control) or received both interleukins but no test compound (positive control). The plates were incubated for 48 hr at 37° C. in a $CO_2$ incubator at which time aliquots (20 μl) were removed for analysis of IFN-γ concentration by ELISA. A quantitative ELISA was developed by coating 96-well plates with an mouse monoclonal antibody against human IFN-γ, 1 μg/ml in phosphate buffered saline (PBS) (Pestka Biological Laboratories), overnight at 4° C. Unbound antibody was washed off by washing three times with PBS. Non-specific antibody binding was blocked with a solution of 1% bovine serum albumin (BSA) and 1% goat serum in PBS (150 μl/well) which was incubated for 2 hr at 37° C. After washing the blocked plates four times with PBS, test samples and dilutions of the IFN-γ standard are added in a final volume of 100 μl/well. Following an overnight incubation at 4° C., the plates are washed four times with PBS, and a polyclonal rabbit antiserum against human IFN-γ (1/10000 dilution—Petska Biological Laboratories) is added. After an additional incubation for 1 hr at 37° C. and four washes with PBS, a polyclonal donkey anti-rabbit detecting antibody, conjugated to horseradish peroxidase (1/700 dilution—Petska Biological Laboratories) is added for 1 hr at 37° C. The plates are then washed four times with PBS and 100 μl of K-blue substrate E(ILISA Technologies, Neogen Corp.) is added until the color in the wells containing the standard curve is sufficiently developed, at which time 100 μl of "Red-stop" solution (ELISA Technologies) is added. The absorbance of the solution within each well of the plate is then read at 650 nm using an ELISA plate reader (Dynatech MR7000). The amount of IFN-γ is calculated by comparing the optical density of the test sample with a standard curve derived from the dilutions of the control IFN-y. The amount of IFN-γ that is induced in the presence of both IL-2 and IL-12 generally ranges from 1200–2000 pg/ml while the amount produced in the absence of IL-12 is generally less than 50 pg/ml. Experimental data are shown in Table 2 which discloses a) the percent inhibition of IFNγ production, relative to a negative control of untreated cells, when the cells have been treated with a bis-compound at a final concentration of 5 μg/ml of the listed bis-compound (%INH or IFNγ) and b) the percent of cells which are viable after the treatment with 5 μg/ml of the various bis-compounds, determined by adding MTS to the media (% Viability). MTS is a chemical chromophore that is metabolized in the mitochondria of viable cells to produce a color which increases in intensity in proportion to the numbers of viable cells. The absorbance of the cell culture can be compared to control cultures in order to determine the percent viability.

TABLE 2

| Compound ID # | % INH of IFNγ | % Viability |
|---|---|---|
| 8296 | 103 | 37 |
| 8302 | 95 | 100 |
| 51850 | 77 | 97 |
| 51851 | 86 | 107 |
| 51852 | 109 | 105 |
| 51853 | 104 | 104 |
| 52782 | 102 | 116 |
| 53433 | 97 | 26 |
| 53437 | 74 | 85 |
| 53529 | 18 | 88 |
| 53553 | 62 | 72 |
| 54003 | 101 | 85 |
| 54004 | −37 | 99 |
| 54005 | 96 | 30 |
| 54007 | 95 | 26 |
| 54008 | 91 | 69 |
| 54010 | 69 | 97 |
| 54015 | 96 | 34 |
| 54016 | 26 | 98 |

TABLE 2-continued

| Compound ID # | % INH of IFNγ | % Viability |
|---|---|---|
| 54018 | 55 | 92 |
| 54019 | 77 | 101 |
| 54020 | 69 | 95 |
| 54025 | 78 | 48 |
| 54028 | 96 | 101 |
| 54036 | 34 | 92 |
| 54039 | 78 | 78 |
| 54042 | 28 | 102 |
| 54044 | 98 | 92 |
| 54046 | 76 | 95 |
| 54048 | 68 | 79 |
| 54050 | 63 | 86 |
| 54053 | 93 | 33 |
| 54054 | 98 | 27 |
| 54055 | 83 | 88 |
| 54056 | 84 | 87 |
| 54058 | 88 | 86 |
| 54059 | 64 | 88 |
| 54062 | 92 | 58 |
| 54063 | 73 | 93 |
| 54064 | 79 | 112 |
| 54094 | 97 | 25 |
| 54099 | 85 | 93 |
| 54109 | 93 | 33 |
| 54113 | 96 | 74 |
| 54114 | 65 | 96 |
| 54346 | 91 | 84 |
| 54471 | 89 | 83 |
| 54472 | 98 | 26 |

As can be seen from the data, several of the bis-compounds were effective at inhibiting IFNγ production while not decreasing the viability of the cells. The data presented were obtained from a single test of each listed compound in the above described assay. Generally, each compound which appears to be of interest, is tested two or more times using the above assay and an average of the data results is calculated. A compound which inhibits IFNγ production by approximately 70% while maintaining cell viability at approximately 70% or higher is considered to be of interest for further screening.

Example 2 Mixed Lymphocyte Reaction

This reaction measures the T cell response to allogenic stimulation by a mismatch of class II histocompatability antigens. This is triggered through the T cell receptor and activates the T cell to secrete and proliferate in response to endogenous IL-2. IFN-γ is also made in response to this stimulation and accumulates in the culture medium. Compounds are tested for their ability to block the proliferation and response to antigenic stimulation as well as their ability to produce IFN-γ as follows. A human B cell ine expressing class II antigen, Namalwa (American Type Culture Collection), is incubated for 2 hr at 37° C. in RPMI-10 containing mitomycin C (50 µg/ml). These cells are washed four times by centrifugation and resuspension ($10^6$ cells/ml) in SF-RPMI medium and are added to the wells of 96-well plate (50 µl/well) as stimulators. Mitomycin treatment prevents these cells from proliferating in the assay. Fresh PBMC are prepared as described above in example 1, but are not activated with PHA. Instead they are resuspended at $10^6$ cells/ml and 100 µl is added per well. Dilutions of test compounds are added (50 µl/well) to give a final volume of 200 µl and the plates are incubated for 6 days at 37° C. During the last 18 hr, $^3$H-thymidine (DuPont-NEN- 1 µCi/well) is added as a measure of cell proliferation, cultures are collected using a cell harvester (Packard), and scintillation fluid is added prior to counting in a Packard Top Count scintillation counter. A sample of medium is also collected for measurement of IFN-γ production prior to the addition of $^3$H-thymidine for use as a negative control.

Figure 1:
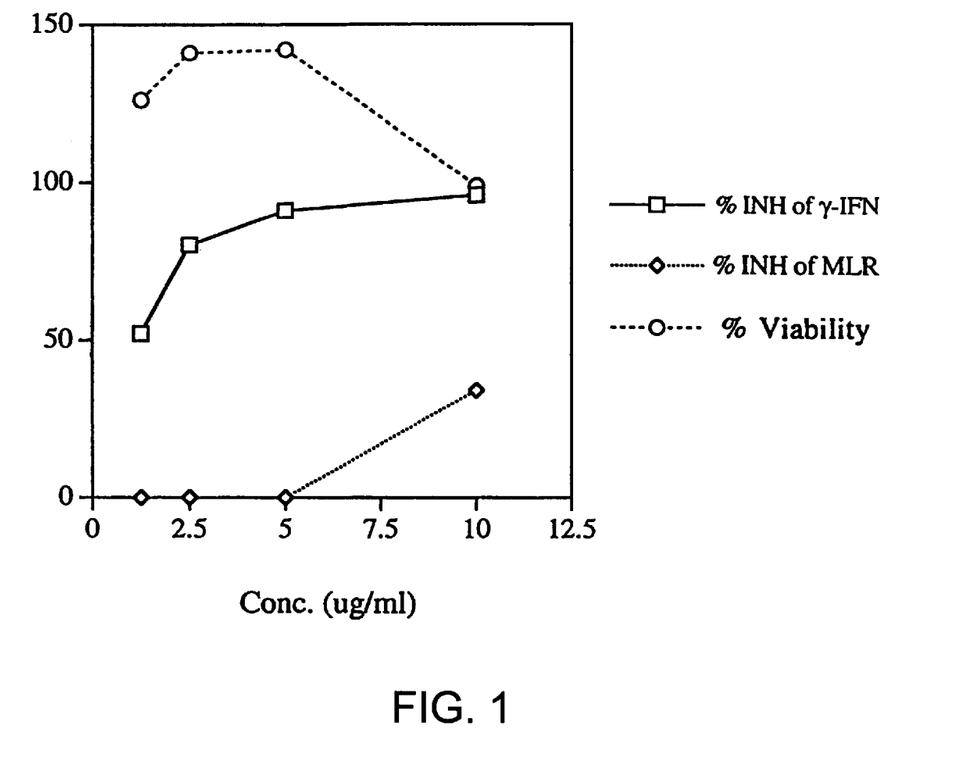
FIG. 1 is a graph depicting the percent inhibition of γ-IFN production (% INH of γ-IFN), the percent inhibition of mixed lymphocyte reaction (% INH of MLR), and the percent viability of the mixed lymphocytes (% Viability) after treatment with bis-phenol compound #51853.
Figure 2:
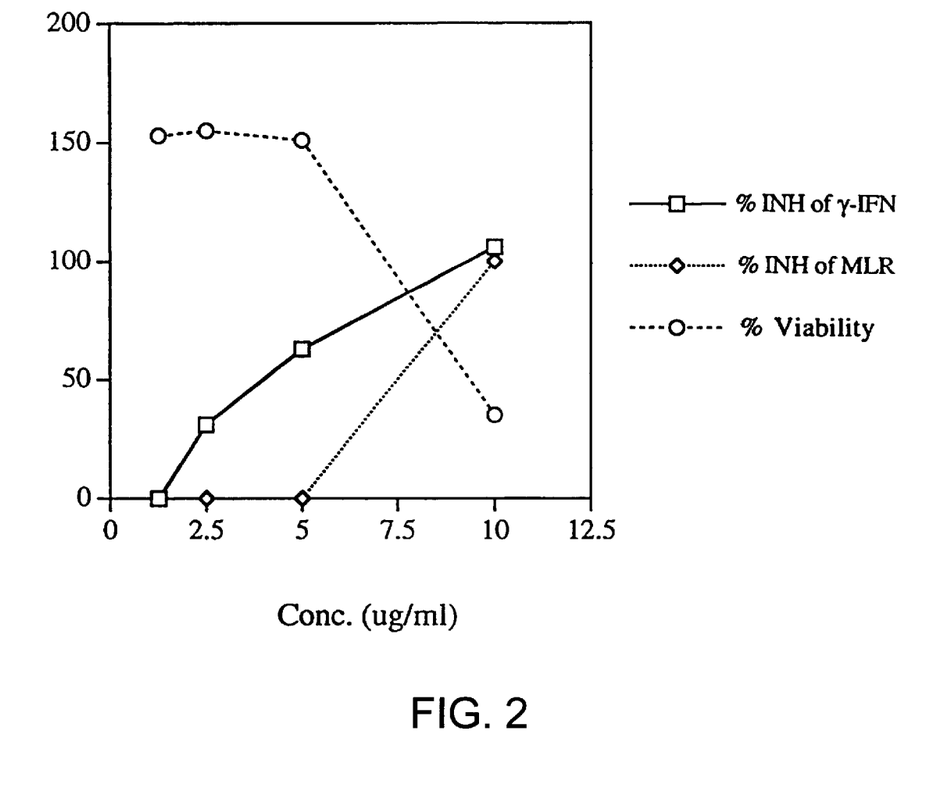
FIG. 2 is a graph depicting the percent inhibition of γ-IFN production (% INH of γ-IFN), percent inhibition of mixed lymphocyte reaction (% INH of MLR), and percent viability of the mixed lymphocytes (% Viability) after treatment with bis-phenol compound #51852.
Figure 3:
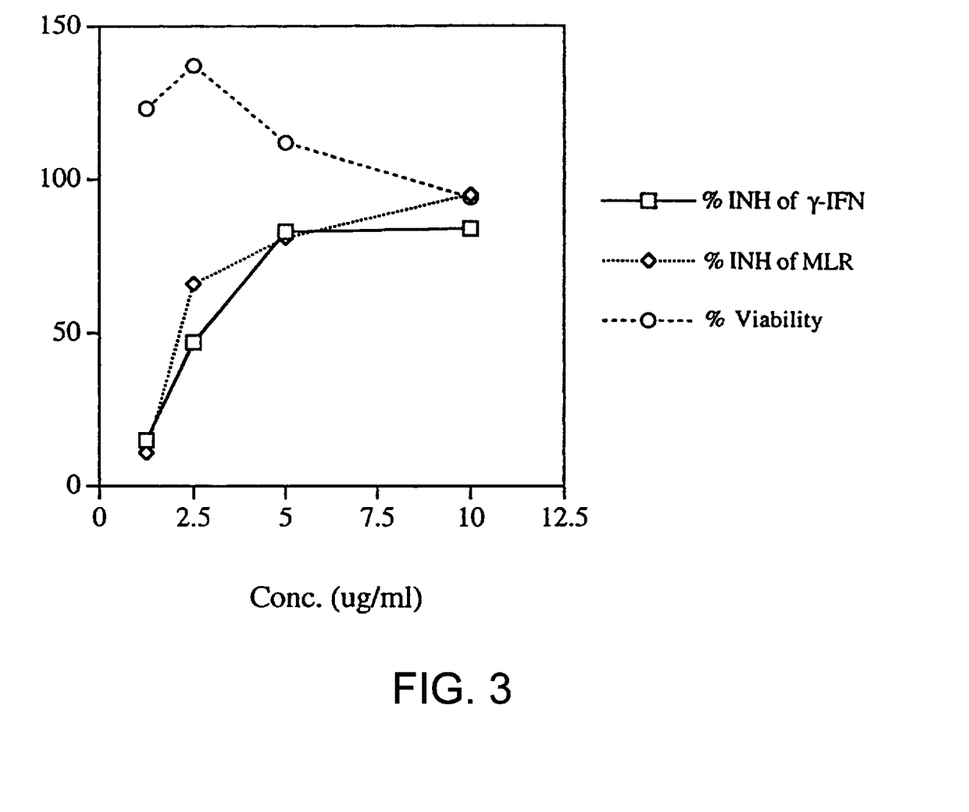
FIG. 3 is a graph depicting the percent inhibition of γ-IFN production (% INH of γ-IFN), percent inhibition of mixed lymphocyte reaction (% INH of MLR), and percent viability of the mixed lymphocytes (% Viability) after treatment with 8-azaguanine (a control to show general immunosuppression).

Representative data are shown in FIGS. 1–3 for two bis-phenol compounds, compounds 51853 and 51852, and for 8-azaguanine, which is another class of inhibitor of IL-12 induced IFN-γ secretion that is a general immunosuppressant. A general immunosuppressant is a compound which inhibits both proliferation and IFN-γ secretion equally. The bis-compounds, on the other hand, are more potent inhibitors of secretion at concentrations that do not effect cell proliferation, and thus are shown to be specific inhibitors of Th1 proliferation.

Example 3 Toxicity of Bis-Compounds

The potential for toxic side effects was assessed following systemic administration of a single dose of bis-compound to mice by an intraperitoneal injection. The results are summarized in Table 3 below.

Toxicity Report

| Comp. | Solution | Inj | Dose mg/kg | Conc. sol. mg/ml | Results | LD50 |
|---|---|---|---|---|---|---|
| 51853 | 20% DMSO | IV | 150 | 10 | Dead | >100 < 150 |
|  | 16% cremaphor |  | 100 |  | Alive |  |
| 52782 | 20% DMSO | IV | 80 | 10 | Dead | <80 |
|  | 16% cremaphor |  |  |  |  |  |
| 54015 | 20% DMSO | IV | 80 | 10 | Alive | >80 |
|  | 16% cremaphor |  |  |  |  |  |
| 54044 | 20% DMSO | IV | 150 | 10 | Alive | >150 |
|  | 16% cremaphor |  | 100 |  | Alive |  |
| 54064 | 20% DMSO | IV | 150 | 10 | Dead | >100 < 150 |
|  | 16% cremaphor |  | 100 |  | Alive |  |
| 54039 | 20% DMSO | IV | 150 | 10 | Dead | <100 |
|  | 16% cremaphor |  | 100 |  | Dead |  |
| 54016 | 20% DMSO | IV | 150 | 10 | Alive | >150 |
|  | 16% cremaphor |  | 100 |  | Alive |  |
| 54028 | 20% DMSO | IV | 150 | 10 | Alive | >150 |
|  | 16% cremaphor |  | 100 |  | Alive |  |
| 51850 | 20% DMSO | IV | 150 | 10 | Alive | >150 |
|  | 16% cremaphor |  | 100 |  | Alive |  |
| 54019 | 20% DMSO | IV | 150 | 10 | Dead | >100 < 150 |
|  | 16% cremaphor |  | 100 |  | Alive |  |
| 54003 | 20% DMSO | IV | 150 | 10 | Dead | >100 < 150 |
|  | 16% cremaphor |  | 100 |  | Alive |  |
| 54046 | 20% DMSO | IV | 150 | 10 | Alive | >150 |
|  | 16% cremaphor |  | 100 |  | Alive |  |
| 54018 | 20% EGME | IV | 150 | 10 | Dead | <100 |
|  | 16% cremaphor |  | 100 |  | Dead |  |
| 54020 | 20% EGME | IV | 150 | 10 | Dead | >100 < 150 |
|  | 16% cremaphor |  | 100 |  | Alive |  |
| 8302 | 20% DMSO | IV | 100 | 10 | Alive | >150 |
|  | 16% cremaphor |  | 150 | 10 | Alive |  |
| 51853 | 20% DMSO | IV | 200 | 15 | Alive | >200 |
|  | 16% cremaphor |  | 150 |  | Alive |  |
| 8302 | 16% cremaphore 20% DMSO | IV | 200 | 15 | Alive 1 Dead 1 | 200 |

Based upon the combined results of the above described examples, a subset of the bis-compounds were identified to be potentially useful as compounds for the manufacture of pharmaceuticals for administration to mammals for the purpose of antagonizing IL-12. It is envisioned that such bis-compounds may be administered to humans orally or parenterally for the treatment of multiple sclerosis. Further that bis-compounds may be used topically for the treatment of skin diseases, such as psoriasis. It is envisioned also that bis-compounds can be used in combination with other immunosuppressive drugs such as Cyclosporin A, for example, in organ transplantation to improve the effectiveness of immune modulation and reduce the dose of Cyclosporin A required, thereby decreasing potential toxicity to the subject 
The currently preferred bis-compounds for formulation as compositions to antagonize IL-12 include the compounds designated as 8302, 51853, 51850, 54020, 54019, 54003, 54028, 54064, 54044, and 54046. These compounds have the chemical structures presented below.

$R_5$ and $R_6$ are selected independently from H, $C_1$–$C_{12}$ branched or linear hydrocarbons, phenyl, phenyl substituted with halo, ntiro; carboxy, alkoxy, hydroxy, alkoxy carbonyl, or alkyl, alkyl substituted with halo, nitro, carboxy, alkoxy, hydroxy, or alkoxy carbonyl, or alkenyl, alkenyl substituted with halo, nitro, carboxy, alkoxy, hydroxy, or alkoxy carbonyl;

and each of $R_1$, $R_2$, $R_3$, $R_4$, $R_7$, $R_8$, $R_9$ and $R_{10}$ which is not $OR_{13}$ is independently hydrogen, halo, or linear or branched lower alkyl.

2. The method of claim 1 wherein said immune cells comprise population of cells in an in vitro cell culture.

3. Method of antagonizing IL-12 comprising contacting immune cells, in an amount sufficient to inhibit IL-12 induced production of IFN-γ, with a bis-compound having the formula wherein at least one of $R_1$, $R_2$, $R_3$, $R_4$, $R_{11}$, and at least one of $R_7$, $R_8$, $R_9$, $R_{10}$, $R_{12}$, is $OR_{13}$, where $R_{13}$ is H or lower alkyl;

$R_5$ and $R_6$ are selected independently from H, $C_1$–$C_{10}$ branched or linear hydrocarbons, phenyl, phenyl substituted with halo, nitro, carboxy, alkoxy, hydroxy, alkoxy carbonyl, or alkyl, alkyl substituted with halo, nitro, carboxy, alkoxy, hydroxy, or alkoxy carbonyl, or alkenyl, alkenyl substituted with halo, nitro, carboxy, alkoxy, hydroxy, or alkoxy carbonyl;

and each of $R_1$, $R_2$, $R_3$, $R_4$, $R_7$, $R_8$, $R_9$, $R_{10}$, $R_{11}$ and $R_{12}$ which is not OH or $OR_{13}$ is independently hydrogen, halo, or linear or branched lower alkyl.

4. The method of claim 3 wherein said immune cells comprise a population of cells in an in vitro cell culture.

5. A method of antagonizing the induction of IFN-γ synthesis in a mammal comprising the step of administering to a mammal the compound of claim 1 or 3 in an amount effective to antagonize IL-12 medicated induction of IFN-γ synthesis.

6. The method of claim 5 wherein said administration is parenteral or oral administration.

7. The method of claim 5 wherein said administration is effective to inhibit the induction of Th1 cells.

8. The method of claim 5 wherein said administration is effective to modulate the induction of Th2 cells.

9. The method of claim 5 wherein said administration is effective to inhibit a cellular immune response.

10. The method of claim 5 wherein said administration is effective to stimulate production of Th2 cytokines including IL-4, IL-5, or IL-10.

* * * * *